United States Patent [19]

Blank et al.

[11] Patent Number: 5,683,713
[45] Date of Patent: Nov. 4, 1997

[54] PHARMACEUTICAL COMPOSITIONS FOR TOPICAL APPLICATION

[76] Inventors: Izhak Blank, 4 Simtat Arnon, Kiryat Ono 55000; Alon Blank, 22a Tamar Street, Haifa, both of Israel

[21] Appl. No.: 736,186

[22] Filed: Oct. 24, 1996

Related U.S. Application Data

[63] Continuation of Ser. No. 579,128, Dec. 27, 1995, abandoned, which is a continuation of Ser. No. 238,075, May 2, 1994, abandoned.

[30] Foreign Application Priority Data

May 4, 1993 [IL] Israel .......................................... 105600

[51] Int. Cl.$^6$ ........................................................ A61F 13/00
[52] U.S. Cl. ..................... 424/449; 424/447; 424/448; 514/946; 514/947; 514/618; 514/706; 514/458
[58] Field of Search ..................................... 424/447, 448, 424/449; 514/946, 947, 458, 618, 706

[56] References Cited

U.S. PATENT DOCUMENTS

| | | | |
|---|---|---|---|
| 4,195,095 | 3/1980 | Sheffner | 424/317 |
| 4,246,278 | 1/1981 | Opitz et al. | 424/301 |
| 4,380,549 | 4/1983 | Van Scott | 424/317 |
| 4,690,683 | 9/1987 | Chien | 604/896 |
| 5,091,171 | 2/1992 | Yu | 424/642 |

FOREIGN PATENT DOCUMENTS

| | | |
|---|---|---|
| 0 002 219 | 6/1979 | European Pat. Off. . |
| 1 946 614 | 3/1971 | Germany . |
| 1 317 773 | 5/1973 | Germany . |

OTHER PUBLICATIONS

"Application of Calcium Thioglycolate to Improve Transdermal Delivery of Theophylline in Rats," by Kazuo Kushida et al., Chem. Pharm. Bull., vol. 32, 1984, pp. 268–274.

Primary Examiner—D. Gabrielle Phelan
Attorney, Agent, or Firm—Keck, Mahin & Cate

[57] ABSTRACT

A pharmaceutical and cosmetical preparation which rapidly penetrates through human skin, and which thus is able to bring about the rapid transdermal penetration of a wide variety of active ingredients. The compounds which enhance the rate of dermal penetration are also anti-oxidative agents and thus protect active substances susceptible to oxidative degradation. Preferred agents enhancing penetration and which protect against oxidation are higher esters and higher amides of thioglycolic acid and of mercaptopropionic acid. The preparations can be in the form of mixtures or there may be prepared chemical compounds which are a combination of the active substance and the said thioacids.

11 Claims, No Drawings

PHARMACEUTICAL COMPOSITIONS FOR TOPICAL APPLICATION

This is a continuation application of Ser. No. 08/579,128, filed Dec. 27, 1995, now abandoned, which is a continuation application of Ser. No. 08/238,075, filed on May 2, 1994, now abandoned.

BACKGROUND OF THE INVENTION

In recent years increased interest has been shown in the development of topically applied medications. In some cases these are targeted to the treatment of various skin diseases and in others they are designed for the transdermal supply of a therapeutic agent. In both cases it is generally desirable that the drug should penetrate through the epidermis into the vascularized layers of the skin.

The main barrier to the penetration of drugs, whether into the skin or all the way through it, is the stratum corneum, also known as the horny layer. This consists of layers of keratinocytes embedded in a matrix of lipid bilayers, its total thickness being only about 15–20 micron. It acts in both directions by preventing dessication of the underlying tissues and also by impeding the entry of noxious substances through the skin into the body.

Keratin, the major component of the dead cells of the horny layer is mostly composed of polypeptides ranging in size from 40000 to 70000 daltons, rich in serine and glycine. A very important structural feature of keratine is the presence of S—S bonds derived from the sulfur-containing diamino acid cystine.

Considerable work has been devoted to find methods and substances capable of enhancing the penetration of drugs through the skin. It has been shown that hydration of the stratum corneum decreases its barrier function. Occlusion has been used to increase hydration and consequently drug penetration. Another method of increasing hydration consists of the use of Sodium pyrrolidone carboxylate and some of its homologs which have been shown to increase the water-binding capacity of the stratum corneum and thus increase the transdermal transport of drugs. The use of occluding bandages and hydrating materials is of limited usefulness for certain specific situations.

Other methods for permeation enhancement are based on the ability of the penetrant to dissolve in and diffuse through the stratum corneum lipids. A number of substances has been used for this purpose, such as the lower alcohols by themselves or mixed with hydrophobic solvents of the n-alkane type. Other solvents have also been mentioned in this context, such as acetone, tetralinhydrofurfuryl alcohol and propylene glycol. All these materials increase somewhat the transdermal flux of various drugs but they also cause irritation and edema and are thus not acceptable for regular application.

Dimethyl sulfoxide (DMSO) a dipolar aprotic solvent which is miscible with both water and organic solvents has the ability to accelerate the skin permeation of a wide variety of compounds, such as steroids and antimycotics. DMSO acts by eluting some components from the stratum corneum. It delaminates the horny layer and denaturates its proteins. This denaturation is irreversible and moreover significant permeation enhancement is obtained only when DMSO is present in excess of about 70%. This raises the danger of toxicological complications. Alkyl homologs of methyl sulfoxide have also been evaluated as potential enhancers of skin permeability. Thus, decyl methyl, sulfoxide enhances the penetration of sodium methotrexate across human skin, but also creates toxicological problems.

Surface-active substances of all types, anionic, cationic and non-ionic have also been investigated as enhancers for drug penetration, as well as a new type of surfactant, 1-dodecylazacycloheptan-2-one also known as Azone.

Urea has been used for many years as a keratolyte and enhancer of drug penetration. This material acts by irreversible degradation of the polypeptide constituents of the skin.

A paper recently published in Japan, describes experimental work in vivo (rats) using a model chemical (6-carboxylfluorescein). By using small concentrations of 2-mercaptoethanol (0.1% w/v) in conjunction with sodium dodecyl sulfate (0.05% w/v), plasma levels of the dye increase 40 times as compared with a control. Pretreatment of the skin with a 4% calcium thioglycolate also increased penetration, but only 9 times as compared to the control. These materials act by reversibly cleaving the S—S cystine bonds which crosslink the keratin structure. Without such crosslinks, the keratin molecules become linear, their solubility parameters change drastically and they become more receptive to the passage of drugs and solvents. They are also much more easily hydrated and plasticized by water molecules. There was no considerable difference on the dye plasma levels between skin where the stratum corneum had been removed mechanically and intact skin treated with the above formulation containing the mercaptan with the surfactant additives. Upon removal of the thio compound reoxidation takes place and the S—S bonds are restored. Using the same principle, dilute solutions of Ammonium thioglycolate have been used for many years for the cold-waving of hair. Increased hydration is obtained by application of the thioglycolate solution to the hair which then becomes plastic and is curled over a suitable mold.

The thioglycolate is then removed by rinsing and fixation of the shape is obtained by treatment with a dilute peroxide solution or with hot air. 2-Mercaptoethanol and the salts of thioglycolic acid are very strong irritants. It is well known that exaggerated use of ammonium thioglycolate may severely weaken and damage the hair. Calcium thioglycolate is actually used as a depilatory. It has been shown to enhance skin penetration of theophylline, but it is also extremely irritating and can cause severe blistering. All these materials have a very unpleasant sulphide odor. For these reasons, they can not be used for topical applications.

SUMMARY OF THE INVENTION

This invention relates to a novel method and compositions for enhancing transdermal penetration of drugs, cosmetics and any other beneficial materials. We have found that certain esters and amides containing a thio group are capable of highly increasing the flux of drugs through the skin without the unpleasant effects related to thioglycolic salts and other materials above mentioned.

In general material containing the —SH group or capable of yielding the —SH group upon biochemical transportation are of potential use in the compositions of this invention.

The thio derivatives found to be most efficacious for this purpose are the esters and amides of thioglycolic acid having the general formula $SH—CH_2—COOR$ and $SH—CH_2CONHR$ where R is alkyl of a molecular weight adequate to reduce the volatility of the compound and impart enough liposolubility to facilitate penetration through the skin.

Such esters and amides of thioglycolic acid are generally non-irritating, even when in contact with the skin for a long time, and due to their low volatility are free of sulphide odor. They are therefore most suitable for topical application. We have demonstrated in-vivo that this type of molecules can open S—S cystine bonds and in-vivo we have shown enhanced penetration of various drugs. Derivatives of mercaptopropionic acid can also be used for the same purpose. The SH moiety in all these compounds is known to act also as an antioxidant and thus assists in prolonging the shelf-life of some of the drugs which are sensitive to this type of degradation and in improving their therapeutic performance.

Preferred esters for use in compositions of this invention are the higher esters of thioglycolic acid, derived from alcohols having more than 8 carbon atoms in the alcohol group. Most preferred are octyl, iso-octyl, dodecyl, stearyl and cetostearyl thioglycolate.

All these are non-irritating, while the lower esters such as methyl or ethyl thioglycolate are irritants. Preferred amides are Dodecyl and Octadecyl thioglycolamide. These amides are new chemical entities and can be prepared by methods well known in the art.

The materials herein described contain the —SH moiety, which is known to act as an antioxidant both in-vitro and in-vivo due to the ability of the —SH group to quench free radicals. Glutathione and similar derivatives containing the —SH moiety, are known to act in-vitro and in-vivo body as antioxidants by capturing free radicals, thus preventing damage to the cell membranes. For instance, it is known that glutathione can regenerate the free radical of Vitamin E, thus allowing it to function again as an antioxidant. In other cases, the presence of the above described thioglycolates and thiopropionates in drug formulations will protect those drugs which are susceptible to oxidation by quenching free radicals formed due to influence of air, light and other external factors.

In some cases it is advantageous to combine a drug with such a thio compound via ester, amide, ether or other non-ionic links. The novel molecules obtained have both enhanced transdermal penetration and stability to oxidation. This is important for instance in the case of tocopherol (Vitamin E) which is one of the most important biological antioxidants. Its —OH group effectively quenches free radicals and there are mechanisms in the body whereby gluthatione regenerates the tocopherol and allows it to function again as a free radical scavenger. Esters of tocopherol containing the —SH group therefore have a combined antioxidant effect obtained when the esterases, present in the tissues, hydrolyze these esters. These new type of molecules are described below.

BRIEF DESCRIPTION OF THE PREFERRED EMBODIMENTS

The invention is illustrated by way of example only, with reference to compositions containing topical fungicides such as Tolnaftate. This is used in the treatment of certain fungal diseases. It has limited penetration through keratin, and this reduces its effect especially in the case of fungal infections affecting the nails (Onycomycosis) where treatments last for months due to the fact that the pathogens reside deep inside the keratin layers.

Another example of the application of the compositions of this invention is in topical therapy using Non-Steroidal Anti-Inflammatory Drugs (NSAID), such as Indomethacin. Inflammation and pain are generally localized in the joints and other defined areas, but treatment with these drugs is generally systemic via per-os application, which causes gastric irritation and other side-effects. Topical application to the inflamed area is of benefit, except that in many cases the rate to penetration of the drug through the skin is not adequate to sustain therapeutic levels.

With the assistance of the enhancers of this invention flux can be increased considerably and plasma therapeutic levels can be achieved.

Still another example of the uses of this invention are new tocopherol derivatives having enhanced transdermal penetration and antioxidant effect.

There are many drugs and cosmetic materials which can be used in conjunction with the penetration enhancers of the invention, the only condition being that there is no chemical incompatibility between drug and enhancer. A partial list of the drugs comprises: propranolol, nitroglycerine, progesterone, medroxyprogesterone, prednisone, prednisolone, testosterone, estradiol, estriol, estrone, aspirine, salicylates and salicylate esters, salicyl alcohol; Non-steroidal anti-flammatories: indomethacin, diclofenac sodium, ibuprofen, piroxicam, ketorolac; antimycotics such as tolnaftate, tolciclate, tioconazole, sulbentine, ketoconazole, itraconazole saperconazole, fluconazole, oxiconazole, naftifine, terbinafine, miconazole econazole, clotrimazole, ciclopiroxolamine, terconazol, metrodinazole; other drugs such as sulfadiazine, aclometasone dipropionate, clobetasol propionate, albuterol, metrodinazole, cytotoxic agents, pyridoxine, allantoin and many other materials of potential topical application for therapeutic or cosmetic reasons, where penetration through the stratum corneum is of importance.

Compositions of the invention for topical application contain at least one of the above defined esters or amides, resulting in enhanced skin penetration with simultaneous antioxidant effect. The composition may also include various surfactants, solvents, film-forming polymers, thickeners, occluders and emollients.

Solvents and carriers suitable for the materials of this invention are: alcohols, esters, vegetable and mineral oils, waxes, and related materials suitable for pharmaceutical and cosmetic applications. The invention is illustrated by way of example only, with reference to compositions containing topical fungicides such as Tolnaftate. This is used in the treatment of certain fungal diseases. It has limited penetration through keratin, and this reduces its effect especially in the case of fungal infections affecting the nails (Onycomycosis), where treatments last for many months due to the fact that the pathogens reside deep inside the keratin layers.

Another example of the application of the compositions of this invention is in topical therapy using Non-Steroidal Anti-Inflammatory Drugs (NSAID), such as Indomethacin. Inflammation and pain are generally localized in the joints and other defined areas, but treatment with these drugs is generally systemic via per-os application of tablets. This causes gastric irritation and other side-effects. Topical application to the inflamed area could be of benefit, except that in many cases the rate of penetration of the drug through the skin is not enough to sustain therapeutic levels.

With the assistance of the enhancers of this invention flux can be increased considerably and plasma therapeutic levels can be achieved.

The invention is illustrated by the following examples, but not limited to these:

EXAMPLE 1—IN-VITRO DEMONSTRATION OF THE REACTION

A test was made to check whether the presence of a thioglycolate ester will cause conversion of Cystine into Cysteine:

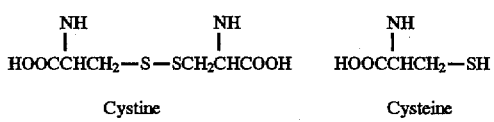

Cystine — Cysteine

In a three necked flask (100 ml), under nitrogen were added 10 ml of water (pH 7.2), 200 mg cystine and 200 mg, of iso-octyl thioglycolate and stirred at room temperature for 24 hours. The reaction was followed by TLC using Silica-Gel precoated plates. As an eluant a mixture of $BuOH:H_2O:AcOH$ in a 10:1:5 ratio respectively was used. The plates were developed by spraying a solution of 5% Ninhydrine in ethanol and heating. After 6 hours a spot corresponding to cysteine was formed and this spot grew as a function of time. This showed clearly the conversion of the disulfide to the mercaptan. A control experiment was made under the same conditions but without the Thioglycolate ester. After 20 hours at room temperature no cysteine could be detected.

EXAMPLE 2—DODECYLAMIDE OF THIOGLYCOLIC ACID 20 gr. of Iso-Octyl Thioglycolate and 18 g. of Dodecylamine were mixed at room temperature under a nitrogen atmosphere. The mixture solidified into a white mass, releasing some heat. The material was dissolved in hot ethanol and it crystallized on cooling. It was filtered and dried; yield 12 g. The melting point was 111° C. This is a new compound having the formula:

$SH-CH_2CONHC_{12}H_{25}$     m.w. 259

Elementary analysis showed the following results:

|   | Calculated (%) | Found (%) |
|---|---|---|
| C | 64.86 | 65.43 |
| H | 11.20 | 10.80 |
| N | 5.40 | 5.44 |
| S | 12.35 | 12.45 |

EXAMPLE 3—OCTADECYLAMIDE OF THIOGYLCOLIC ACID 20 gr. of iso-octyl thioglycolate and 27 g. of melted octadecylamine were mixed under a nitrogen atmosphere. The mixture solidified with a slight release of heat. Washed twice with ethanol and filtered. Obtained 28 g. of an off-white material with a melting point of 104° C. This is a new compound having the formula:

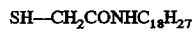

$SH-CH_2CONHC_{18}H_{27}$

Elementary analysis showed the following results:

|   | Calculated (%) | Found (%) |
|---|---|---|
| C | 69.97 | 71.04 |
| H | 11.95 | 11.85 |
| N | 4.08 | 4.25 |
| S | 9.33 | 8.26 |

EXAMPLE 4

A number of ointments and gels for topical applications were prepared including some of the above materials. White Petrolatum was used in the preparation of ointments. For gels, the preferred solvent used ethanol. Various excipients were added to these formulations, such as isopropyl myristate, hydroxpropyl cellulose, cetyl alcohol, stearic acid, fumed silica and acrylic polymers. A summary of such preparations is given below. Figures indicate percentage by weight.

Formulation

A) Iso-Octyl Thioglycolate 1; Tolnaftate 1; diluent: ethanol.

B) Iso-Octyl Thioglycolate 28.9; Triazole fungicide 0.96; diluent: vaseline.

C) Dodecylamide of Thioglycolic acid 5; Triazole fungicide 1; solvent: ethanol.

D) Iso-Octyl Thioglycolate 4; Indomethacin 2; diluent: ethanol.

EXAMPLE 5

Six patients affected by Tinea Pedis were treated by daily application of the composition of example 4A. Three patients had severe fungal infection in the interdigital space, resulting in itching, reddening and descamation. After 3 days of treatment the itching disappeared completely and so did the reddening and descamation after 8 days. The other patients suffered from formation of vesicles, itching and descamation on the sole and nearby area (athlete's foot). After one week treatment improvement was noticed in all the patients and itching disappeared. After anther week, descamation stopped completely.

EXAMPLE 6

Three patients suffering of Onycomycosis were treated by applying the preparation of example 4A twice a day on and around the nails. Once a week the upper keratinous layer was removed. After one month of treatment two of the patients showed considerably clearing of the thickening at the distal edge of the nails and the yellow coloration disappeared. After two months of treatment there was an almost complete disappearance of thickening in all three patients.

EXAMPLE 7

Three Onycomycosis patients were treated with the preparation 4B. After 3 to 6 weeks of treatment, a new healthy nail growth was observed. Patients did not complain of any irritation or other side effects.

EXAMPLE 8

Gel 4C was topically applied once a day by three patients suffering on onycomycosis. All of them reported prompt disappearance of itching and reddening. After four weeks considerable clearing of colour and reduction of distal thickening was observed.

EXAMPLE 9—ANIMAL STUDIES WITH NSAID.

Test animals were female white rats of about 200 g weight. The rats were anesthesized and their backs shaven. A surface of 11×4 cm. was marked and to this a measured amount of about 600 mg. of the gel was applied and spread out informly with a spatula. The gel dried after about 3 minutes, leaving an invisible film on the skin. Nearly one hundred rats were used in various tests designed to optimize transdermal penetration and check any side effects. Rats were decapitated at various times after application and the blood samples were analyzed for Indomethacin content.

In a comparative test the following materials were used:
1) Gel containing 5% Indomethacin without enhancer
2) Placebo gel
3) Gel as per example 4D containing 5% Indomethacin and 4% enhancer (Iso-octyl thioglycolate).

Results obtained are summarized in the table as microgram Indomethacin per ml plasma:

|  | Time after application (hours) | | |
| --- | --- | --- | --- |
| Material | 3 | 6 | 24 |
| 1 | 2.4 | 3.5 | 20.0 |
| 2 | — | 0.5 | — |
| 3 | 5.5 | 16.0 | 30.7 |

After six hours the levels produced by the preparation containing the enhancer are 4.5 times higher than those of the preparation, with a higher drug content but without enhancer.

EXAMPLE 10

A gel based on hydroxypropyl cellulose in ethanol was prepared with the addition of various emollients and containing 1% of beta-Estradiol as the active ingredient. From this base four different formulations were made up as follows:

I gel base without enhancer
II gel base with addition of 5% Iso-Octyl Thioglycolate
III gel base with addition of 5% Dodecylamide of Thioglycolic acid.
IV gel base with addition of 5% Octadecylamide of Thioglycolic acid.

Male rats weighing 320–350 gr. each were used in this test. An area in the back of the rats was shaven and to it were applied 0.15 ml of the gel and spread uniformly with a spatula. The rats were kept in separate cages and sacrificed after two hours. The whole blood was sent for analysis. Results are given in pg/ml plasma.

| Gel | |
| --- | --- |
| I | 150 |
| II | 630 |
| III | 2200 |
| IV | 550 |

In this particular test gel number III gave the best result.

EXAMPLE 11

Tocopherol (Vitamine E) acetate was formulated in the form of a gel or ointment as per the following compositions, given as % by weight:

| Material: | I | II* | III | IV | V | VI |
| --- | --- | --- | --- | --- | --- | --- |
| Hydroxypropyl cellulose, pharm. grade (2% in EtOH) | 75 | 75 | 75 | 75 | 70 | — |
| Propylene glycol | 5 | 5 | 5 | 5 | 5 | 5 |
| Cetyl alcohol | 5 | 5 | 5 | 5 | 10 | — |
| Isopropyl Myristate | 3 | 3 | 3 | 3 | 3 | 3 |

-continued

| Material: | I | II* | III | IV | V | VI |
| --- | --- | --- | --- | --- | --- | --- |
| Thioglycol dodecylamide | 5 | — | — | — | — | — |
| Iso-Octyl thioglycolate | — | — | — | 5 | — | — |
| Dilauryl thiodipropionate | — | — | 5 | — | — | 5 |
| Vitamin E Acetate | 2 | 2 | 2 | 2 | 2 | 2 |
| White Petrolatum | — | — | — | — | — | 85 |

*Formulation without penetration enhancer, used for comparison

These formulations were tested as antioxidants in biological systems, using rat liver microsomes in the standard test for measure this effect. The best formulations were found to be numbers I and IV

EXAMPLE 12—THIOGLYCOLIC ESTER OF TOCOPHEROL

This preparation was made in two steps. In the first step, to a mixture of tocopherol (3 gr.) and triethylamine (12 ml) in 25 ml. of methylene chloride, were added two equivalents of chloroacetyl chloride, dissolved in 15 ml. of methylene chloride. The reaction mixture was stirred at room temperature, water was added and resulted in two layers. The organic layer was washed with dilute HCl, water and dried over magnesium sulfate. The solvent was removed under reduced pressure and the crude material was purified by passing over a silica column. The product was eluted with a methylene chloride-hexane mixture yielding the chloroacetyl ester in nearly quantitative yield (3 gr.). The second step consists of the preparation of tocopherol thioglycolate. To a 3-necked flask were added potassium sulfide (10 gr.) and 20 ml. of dry THF. Into the THF were bubbled dry Hydrogen Sulfide. To this mixture were added 4 gr. of ester as per step one. The reaction was carried to completion and then 50 ml. of a saturated sodium bicarbonate solution were added. The product was extracted from the reaction mixture by methylene chloride and dried over magnesium sulfate. The crude product was purified by chromatography over silica gel to give a colourless and odorless oil in close to quantitative yield. The material was characterized by means of NMR spectra, GC—MS and High Resolution Mass Spectroscopy.

EXAMPLE 13—THIOPROPIONIC ESTER (MERCAPTOPROPIONIC ESTER) OF TOPOCPHEROL

Two equivalents of Chloropropionyl chloride, prepared from chloropropionic acid and thionyl chloride, were reacted with one equivalent of tocopherol dissolved in methylene chloride/pyridine. Washed as in example 12 and purified by passing over a silica column (70–230 mesh). Structure of this ester was confirmed by NMR.

We claim:
1. Pharmaceutical and cosmetic compositions for enhancing transdermal penetration which provide for antioxidative protection against degradation of oxidation sensitive active ingredients, comprising a non-irritating combination of a higher ester or higher amide of thioglycolic acid or mercaptopropionic acid of the general formula:

where n is 1 or 2; Q is —OR or —NHR, R being an alkyl chain from 8 to 32 carbon atoms, a pharmaceutically active substance or cosmetically active substance and at least one member selected from the group consisting of solvents, thickeners, emollients, surfactants, film-forming polymers and occluders.

2. A composition according to claim 1, comprising a mixture containing an ester formed from the thioglycolic acid or thiopropionic acid and an active substance which has at least one reactive hydroxy group.

3. A composition according to claim 1, where the amides are amides of thioglycolic acid or mercaptopropionic acid having 8 to 32 carbon atoms in the R group of —NHR.

4. A composition according to claim 1, where the active ingredient is selected from fungicides, non-steroidal anti-inflammatory agents, hormones and vitamins.

5. A composition according to claim 2, where the ester is an octyl, iso-octyl, dodecyl or octadecyl ester of thioglycolic acid or of mercaptopropionic acid.

6. A composition according to claim 4, where the active substance is selected from tolnaftate, indomethacine and tocopherol.

7. A composition according to claim 1, containing from 0.1 to 20 weight-% of thioglycolate monododecylamide or thioglycolate mono-octadecylamide as antioxidation protective agent of pharmaceuticals and cosmetic agents.

8. A compound of the formula $$HS-(CH_2)_n-CONHQ'$$

where n is 1 or 2, and where Q' is $$-C_{12}H_{25} \text{ or } -C_{18}H_{37}.$$

9. A compound of the formula:

$$HS-(CH_2)_n-COR^1$$

where $R^1$ is a tocopheryl residue and n is 1 or 2.

10. A method for enhancing transdermal penetration of a pharmaceutically active substance or a cosmetically active substance which provides antioxidative protection against degradation of oxidation sensitive active ingredients, comprising applying a non-irritating combination of a higher ester or higher amide of thioglycolic acid or mercaptopropionic acid of the general formula:

$$HS-(CH_2)_nCOQ$$

where n is 1 or 2; Q is —OR or —NHR, R being an alkyl chain from 8 to 32 carbon atoms, a pharmaceutically active substance or cosmetically active substance and at least one member selected from the group consisting of solvents, thickeners, emollients, surfactants, film-forming polymers and occluders.

11. A method according to claim 10 comprising applying the composition in a patch which contacts the skin.

* * * * *